United States Patent [19]

Yasuda et al.

[11] 4,258,563
[45] Mar. 31, 1981

[54] GAS SENSOR

[75] Inventors: Eturo Yasuda; Yoshihiro Segawa, both of Okazaki; Minoru Ohta, Anjo, all of Japan

[73] Assignee: Nippon Soken, Inc., Nishio, Japan

[21] Appl. No.: 953,955

[22] Filed: Oct. 23, 1978

[30] Foreign Application Priority Data

Dec. 16, 1977 [JP] Japan .................. 52-152271

[51] Int. Cl.³ .................................. G01N 27/12
[52] U.S. Cl. .................................. 73/23; 123/489
[58] Field of Search .............. 73/23, 27 R; 23/232 E; 422/98; 123/32 EE, 119 EC; 60/276

[56] References Cited

U.S. PATENT DOCUMENTS

| 3,868,846 | 3/1975 | Kushida et al. | 73/27 R |
| 3,932,807 | 1/1976 | Wilson | 73/23 |
| 4,063,447 | 12/1977 | Mathison | 73/27 R |
| 4,112,356 | 9/1978 | Toy | 73/27 R |
| 4,147,513 | 4/1979 | Bienkowski et al. | 73/23 |

Primary Examiner—Stephen A. Kreitman
Attorney, Agent, or Firm—Cushman, Darby & Cushman

[57] ABSTRACT

A gas sensor including a gas sensing element whose electrical resistance varies in accordance with the gas composition in the exhaust gas, especially the oxygen content in the exhaust gas, and a reference resistor connected in series with the gas sensing element. A predetermined voltage is applied across the series circuit of the gas sensing element and the reference resistor to detect the gas composition in the exhaust gas by a voltage at the junction point of the gas sensing element and the reference resistor. The gas sensor further comprises a circuit for monitoring the voltage at the junction point and another circuit responsive to the monitoring circuit to change the resistance of the reference resistor so that when the voltage at the junction point exceeds the predetermined range, the resistance of the reference resistor is changed such that the voltage at the junction point may change within the predetermined range in the state after the reference resistor is changed to ensure that the voltage at the junction point properly indicates the gas composition even if the resistance of the gas sensing element changes with the operating temperature of the gas sensing element or with time.

3 Claims, 7 Drawing Figures

GAS SENSOR

BACKGROUND OF THE INVENTION

The present invention relates to a gas sensor, and more particularly to a gas sensor for detecting the gas composition of gas exhausted from an engine, for enhancing, for example, the efficiency of a catalytic converter.

Heretofore, an exhaust gas sensor has been proposed which comprises a gas sensing element made of a metal oxide semiconductor such as titanium oxide etc., having an electrical resistance which changes depending on the relative gas environment, and a comparator which connects the gas sensing element in series with a fixed reference resistor. This arrangement converts the resistance of the gas sensing element to a voltage and compares that voltage with a predetermined reference voltage to produce a gas detection signal.

However, in the prior art gas sensor, since the fixed reference resistor is connected in series with the gas sensing element, an error in the gas composition detection may occur. Furthermore gas composition detection may become impossible if the electrical resistance characteristic of the gas sensing element changes with operating temperature or with time.

SUMMARY OF THE INVENTION

In accordance with the present invention, the resistance of the reference resistor is made variable and it is set such that the voltage at the junction point of the reference resistor and the gas sensing element changes within a predetermined range under normal operating conditions. The voltage at the junction point is monitored and when it exceeds the predetermined range (due to operation temperature variation, variation over time, or the like), the resistance of the reference resistor is changed such that the voltage at the junction point falls within the predetermined range. With this arrangement, the voltage at the junction point properly indicates the gas composition even if the resistance of the gas sensing element changes with the change of the operating temperature of the gas sensing element or by the lapse of time. Thus, according to the present invention, gas detection occurs satisfactorily even if the electrical resistance characteristic of the gas sensing element changes.

It is, therefore, an object of the present invention to provide a gas sensor which overcomes the problems encountered in prior art sensors and which is capable of properly detecting gas composition irrespective of changes in the electrical resistance characteristic of the gas sensing element caused by changes of operating temperature or by the lapse of time.

DESCRIPTION OF THE PREFERRED EMBODIMENTS

Figure 1:
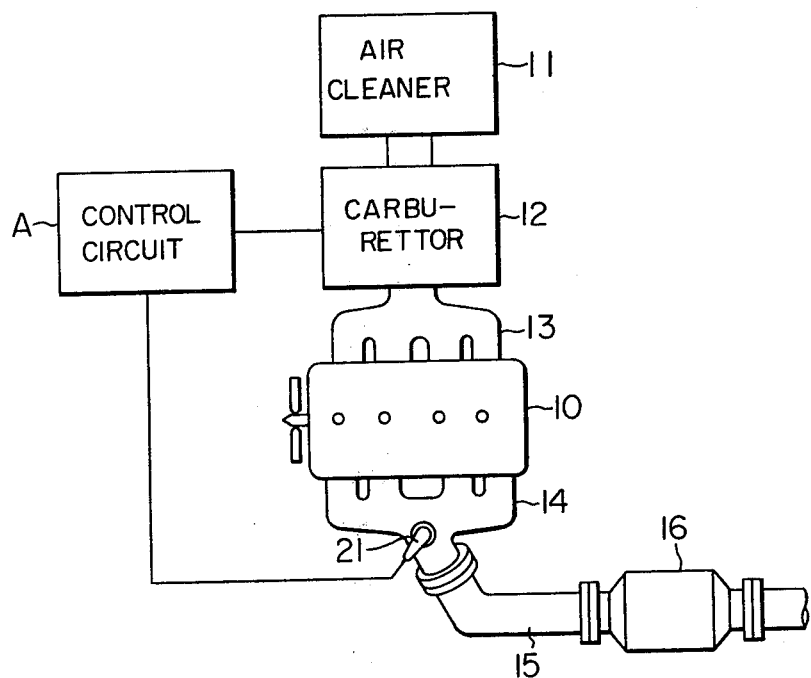
FIG. 1 shows an overall configuration illustrating one embodiment of the present invention.

The present invention will now be explained in detail in connection with the preferred embodiments thereof. FIG. 1 shows a system to which the present invention is applied, including an engine 10 of a well-known spark ignition type engine, a suction system comprising an air cleaner 11, a carburetor 12 and a suction manifold 13, and an exhaust system comprising an exhaust manifold 14, an exhaust tube 15 and a three-way catalytic converter 16.

The carburetor 12 includes a known air-fuel ratio regulator to change the air-fuel ratio A/F of the air-fuel gas in accordance with an electrical signal. The three-way catalytic converter 16 purifies $NO_x$, HC and CO at a high purification factor when air-fuel mixture of approximately stoichiometric air-fuel ratio is supplied engine 10 and it includes a known pellet type or honeycomb-shaped catalyst.

The gas sensor comprises a gas sensing element 21 mounted at a neck portion of the exhaust manifold 14 and a control circuit A for providing an electrical signal to the carburetor 12.

Figure 2:
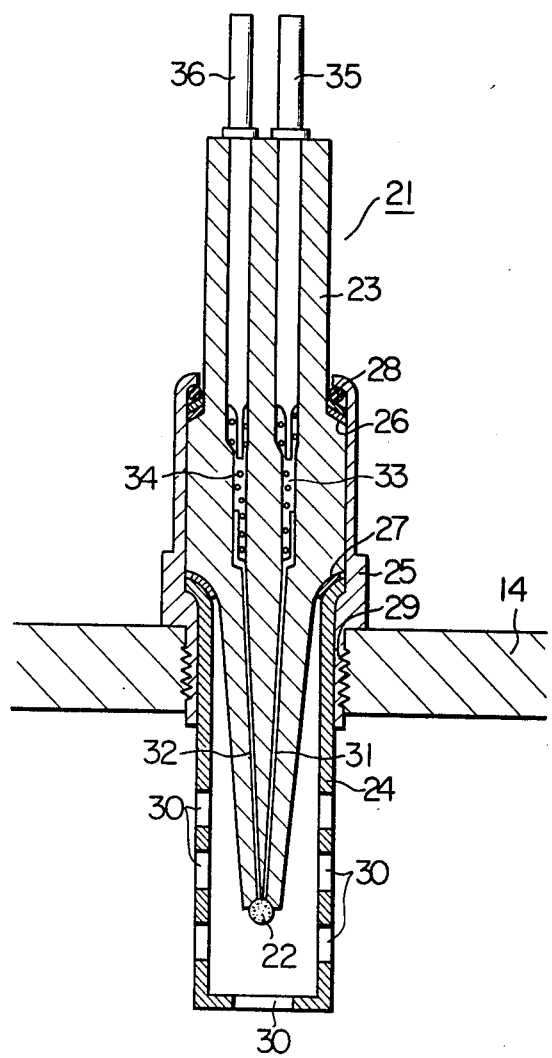
FIG. 2 is a sectional view showing a gas sensing element shown in FIG. 1.

The gas sensor 21 is constructed as shown in FIG. 2, in which a disk-shaped element 22, having an electrical resistance indicative of gas composition in the exhaust gas, especially the density of oxygen, is made of a metal oxide semiconductor such as titanium oxide ($TiO_2$) and carries a catalyst such as platinum (Pt) or rhodium (Rh) on the surface thereof. The element 22 is supported at the recess at an end of a heat-resistive and electrically insulative holder 23 made of a sintered body of alumina, for example.

A protective cover 24 made of a heat resistive metal and a housing 25, are integrally coupled to the holder 23 at tapered portions 26 and 27 through an O-ring 28 and a washer. The holder 23 is attached to the exhaust manifold 14 by a threaded portion 29 of the housing 25.

The protective cover 24 serves to protect the element 22 from the exhaust gas flow and has a number of holes 30 through which the exhaust gas may pass.

Inserted in the element 22 are a pair of platinum electrodes 31 and 32 which are held in the holder 23. The electrodes 31 and 32 are electrically connected to terminal bars 35 and 36, respectively, through conductive glasses 33 and 34. An electrical resistance of the element 22 is measured through the terminal bars 35 and 36.

Figure 3:
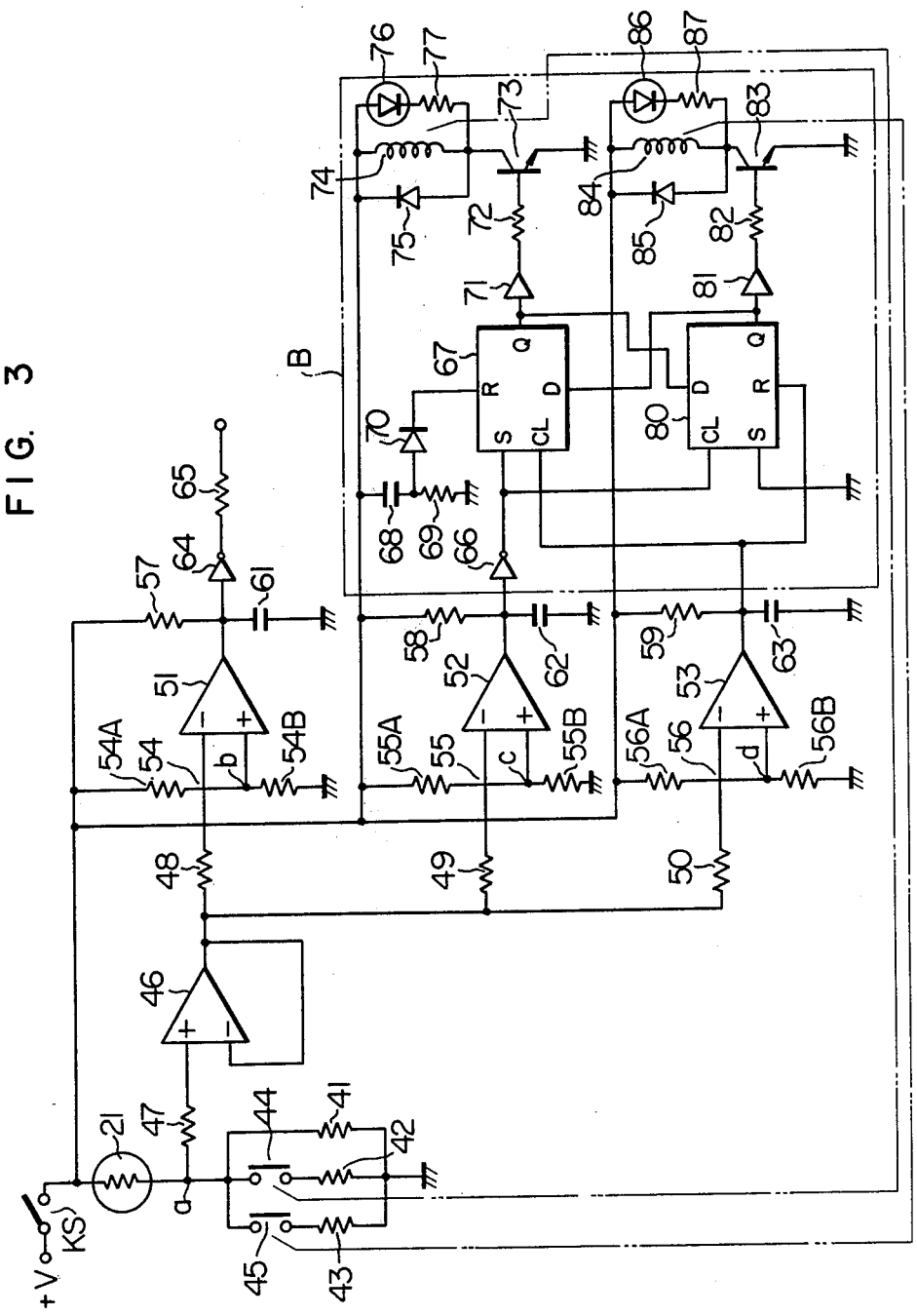
FIG. 3 is an electrical circuit diagram showing a control circuit shown in FIG. 1.

Referring to FIG. 3, the control circuit A is explained. In the control circuit A, a reference resistor means which is connected to the gas sensing element 21 through a voltage dividing point a comprises three parallel-connected reference resistors 41, 42 and 43, to which a constant D.C. voltage V is applied from a battery, not shown, through the gas sensing element 21.

The reference resistors 42 and 43 are connected to the gas sensing element 21 through normally open relay contacts 44 and 45, respectively.

The voltage at point a between the reference resistors 41, 42 and 43 and the gas sensing element 21 is applied to a buffer amplifier 46 which carries out impedance conversion, through an input resistor 47. An output terminal of the buffer amplifier 46 is connected to comparators 51, 52 and 53 through input resistors 48, 49 and 52, respectively.

Reference voltage generators 54, 55 and 56 are each composed of dividing resistors 54A and 54B, dividing resistors 55A and 55B, and dividing resistors 56A and 56B, respectively, and voltage dividing points b, c and d at which reference voltages are produced are connected to the comparators 51, 52 and 53, respectively. The reference voltage generator 54 divides the D.C. voltage V to produce the reference voltage $V_0$, which is applied to the first comparator 51. In the same manner, the reference voltage generators 55 and 56 apply the upper limit reference voltage $V_1$ ($V_1 > V_0$) and the lower limit reference voltage $V_2$ ($V_2 > V_0$) to the second and third comparators 52 and 53, respectively.

The comparators 51, 52 and 53 compare the input voltages with the reference voltages, respectively. When the voltage of the buffer amplifier 46 or the voltage at the dividing point a is smaller than the reference voltage, each of the comparators produces a "1" level output signal and when the voltage at the dividing point a is larger than the reference voltage it produces a "0" level output signal. Noises in the outputs of the comparators 51, 52 and 53 are absorbed by resistors 57, 58 and 59, and capacitors 61, 62 and 63, respectively.

The first comparator 51 produces a gas detection signal in accordance with the change of the electrical resistance of the gas sensing element 21. Connected to the output terminal of the first comparator 51 are an inverter 64 and a resistor 65 in this order so that the output of the first comparator 51 is supplied through the inverter 64 and the resistor 65 to a drive circuit, not shown, from which it is applied to the conventional air-fuel ratio regulator of the carburetor 12 in the conventional manner.

The output signals from the second and third comparators 52 and 53 are applied to a resistance control circuit B which controls the turn-on and turn-off of the relay contacts 44 and 45. The second comparator 52 determines the rise of the operating temperature based on the electrical resistance of the gas sensing element 21. Connected to the output terminal of the second comparator 52 are an inverter 66 and a flip-flop 67 of the resistance control circuit B so that the output of the second comparator 52 is applied through the inverter 66 to a set terminal S of the flip-flop 67 and a clock terminal CL of a flip-flop 80.

The flip-flop 67 is a data type flip-flop (e.g. RCA CD4013A) which operates in accordance with a truth table shown in Table 1.

TABLE 1

| CL | D | R | S | Q |
|---|---|---|---|---|
| ↑ | 0 | 0 | 0 | 0 |
| ↑ | 1 | 0 | 0 | 1 |
| ↓ | X | 0 | 0 | Q |
| X | X | 1 | 0 | 0 |
| X | X | 0 | 1 | 1 |
| X | X | 1 | 1 | 1 | where ↑ and ↓ represent rise and fall of the signal, respectively, X represents that it is independent of the signal, 1 represents the "1" level signal, 0 represents the "0" level signal and Q represents no change in the signal.

Applied to a reset terminal R of the flip-flop 67 is a voltage at the junction point of a capacitor 68 and a resistor 69, through a diode 70. The capacitor 68 and the resistor 69 serve to reset the flip-flop 67 when a switch KS is turned on, that is, to initially reset the flip-flop 67.

An output terminal Q of the flip-flop 67 is connected to a transistor 73 through a signal amplifier 71 and an input resistor 72, to control turn-on and turn-off of the transistor 73.

Connected to the transistor 73 are a relay coil 74 for turning on and off the relay contact 44, a pulsive voltage absorbing diode 75, an indicating light emitting diode 76 and a resistor 77.

The third comparator 53 determines the drop of the operating voltage based on the electrical resistance of the gas sensing element 21, and the output of the third comparator 53 is applied to a clock terminal CL of the flip-flop 67 of the resistance control circuit B and a reset terminal R of the flip-flop 80.

The flip-flop 80 is of the same type as the flip-flop 67 and an output terminal Q thereof is connected to a data terminal D of the flip-flop 67, and a data terminal D of the flip-flop 80 is connected to the output terminal Q of the flip-flop 67. The output terminal Q of the flip-flop 80 is also connected to a transistor 83 through a signal amplifier 81 and an input resistor 82, to control turn-on and turn-off of the transistor 83.

Connected to the transistor 83 are a relay coil 84 for turning on and off the relay contact 45, a pulsive voltage absorbing diode 85, a light emitting diode 86 for indication and a resistor 87.

In the arrangement described above, the electrical resistance of the gas sensing element 21 changes in accordance with the gas composition of the exhaust gas exhausted from the engine 10, especially the oxygen content thereof. Since the gas composition of the exhaust gas changes in accordance with the air-to-fuel ratio A/F of the mixture of air and fuel supplied to the engine 10 from the carburettor 12, the electrical resistance R of the gas sensing element 21 changes in response to the air-to-fuel ratio A/F in a manner shown by curves $T_1$, $T_2$ and $T_3$ in FIG. 4.

Now, when starting the engine the voltage at the voltage dividing point a is at a voltage level which is lower than both the upper and lower limit reference voltages $V_1$ and $V_2$ at the dividing points c and d, therefore both the second and third comparators 52 and 53 produce the "1" level signals.

As a result, the "0" level signal which has been inverted by the inverter 66 is applied to the set terminal S of the flip-flop 67, and a "1" level signal is applied to the reset terminal R for a predetermined period for the initially resetting capacitor 68. Accordingly, a "0" level signal is produced from the output terminal Q of the flip-flop 67. On the other hand, a "0" level signal is normally applied to the set terminal S of the flip-flop 80 and the "1" level signal from the third comparator 53 is applied to the reset terminal R. Accordingly, a "0" level signal is produced from the output terminal Q of the flip-flop 80.

As a result, the transistors 73 and 83 are both turned off and the relay contacts 44 and 45 are held off so that the total electrical resistance of the reference resistor means is equal to the resistance $R_A$ of the reference resistor 41. The resistance $R_A$ has been set such that the voltage at the dividing point a changes between the upper and lower limit reference voltages $V_1$ and $V_2$.

As the temperature rises the electric resistance of the gas sensing element reduces and the voltage at the voltage dividing point a becomes higher than the lower limit reference voltage at the dividing point d. However, even when the reset signal for the flip-flop 80 becomes 0, the output of the flip-flop 80 remains still 0. Meanwhile the electric resistance value of the gas sensing element becomes to cross $R_A$ and the control of rich and lean as described below begins.

Figure 4:
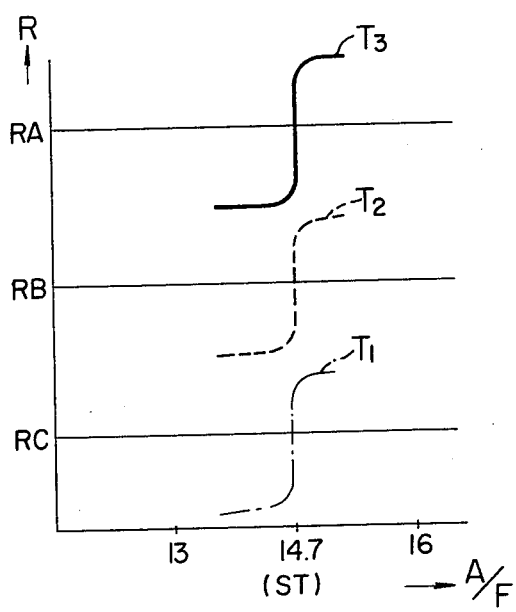
FIGS. 4 and 5 are graphs showing electrical resistance of the gas sensing element.

When the air-to-fuel ratio A/F of the mixture of air and fuel supplied to the engine 10 exceeds a preset value or a stoichiometric air-to-fuel ratio ST, the electrical resistance R of the gas sensing element 21 becomes larger than the reference resistance $R_A$ as shown in FIG. 4. As a result, the voltage at the dividing point a becomes smaller than the reference voltage $V_0$ at the dividing point b so that the first comparator 51 produces a "1" level gas detection signal, which is fed through the inverter 64, the resistor 65 and the drive circuit to the air-to-fuel ratio regulator of the carburetor 12 to reduce the air-to-fuel ratio A/F of the mixture of air and fuel supplied to the engine 10 to the stoichiometric air-to-fuel ratio ST.

On the other hand, when the air-to-fuel ratio A/F becomes smaller than the stoichiometric air-to-fuel ratio ST, the resistance R of the gas sensing element 21 becomes smaller than resistance $R_A$ of the reference resistor as shown in FIG. 4. As a result, the voltage at the dividing point a becomes larger than the reference voltage $D_0$ at the dividing point b so that the first comparator 51 produces a "0" level gas detection signal, which is fed through the inverter 64, the resistor 65 and the drive circuit to the air-to-fuel ratio regulator of the carburetor 12 to increase the air-to-fuel ratio A/F of the mixture of air and mixture supplied to the engine 10 to the stoichiometric air-to-fuel ratio ST.

When the operating temperature of the gas detecting element 21 rises to an intermediate temperature $T_2$, the electrical resistance characteristic of the gas sensing element 21 shifts from the curve $T_3$ to the curve $T_2$ in FIG. 4 and changes at an intermediate level. As a result, the voltage at the dividing point a no longer changes between the upper and lower reference voltages $V_1$ and $V_2$ at the dividing points c and d but the voltage at the dividing point a becomes higher than the upper limit voltage $V_1$. Accordingly, both the second and third comparators 52 and 53 produce "0" level signals.

Accordingly, the flip-flop 67 receives at the set terminal S thereof the "1" level signal which has been inverted by the inverter 66 and receives at the reset terminal R thereof the "0" level signal a predetermined time after the turn-on of the switch KS. As a result, the "1" level signal is produced from the output terminal Q of the flip-flop 67.

On the other hand, the flip-flop 80 receives the "b" level signals at the set terminal S and the reset terminal R thereof, the "1" level signal at the clock terminal CL thereof and the "1" level signal from the terminal Q of the flip-flop 67 at the data terminal D. Since there is a slight time delay from the rise of the signal applied to the clock terminal CL of the flip-flop 67 from the "0" level to the "1" level before the Q output of the flip-flop 67 is inverted from the "0" level to the "1" level and the inverted "1" level output is applied to the data terminal D, the flip-flop 80 produces the "0" level signal from the output terminal Q.

As a result, only the transistor 73 is turned on to turn on only the relay contact 44 so that the total electrical resistance of the reference resistor means becomes equal to be $R_B$ which is the resistance of a circuit made by connecting the reference resistors 41 and 42 in parallel, that is, $$R_B = \frac{R41 \cdot R42}{R41 + R42} < R_A.$$

The resistance $R_B$ has been set such that the voltage at the dividing point a changes between the reference voltages $V_1$ and $V_2$. In this manner, as the electrical resistance of the gas sensing element 21 decreases, the electrical resistance of the reference resistor means also decreases, and the gas composition detection by the first comparator 51 is conducted properly as it is so made in the operating temperature of $T_3$.

When the total resistance of the reference resistor means becomes $R_B$, the voltage at the dividing point a becomes lower than the upper limit voltage $V_1$ at the dividing node c and the output of the second comparator 52 is inverted to the "1" level but the Q output of the flip-flop 67 is held at the "1" level because an "0" level signal is being applied to the reset terminal R of the flip-flop 67.

Thereafter, if the operating temperature of the gas sensing element further rises to about the highest operating temperature $T_1$, the electrical resistance R of the gas sensing element 21 shifts to the curve $T_1$ shown in FIG. 4 and changes at a further lower level. As a result, the voltage at the dividing point a again becomes higher than the upper limit reference voltage $V_1$ at the dividing point c so that the second comparator 52 again produces the "0" level signal, like the third comparator 53.

Accordingly, the input signal to the clock terminal CL of the flip-flop 80 rises from the "0" level to the "1" level, and since the "0" level signal is applied to both the set terminal S and the reset terminal R and the "1" level signal is applied to the data terminal D from the output terminal Q of the flip-flop 67, the input signal to the data terminal D, that is, the "1" level signal is produced from the output terminal Q.

As a result, the transistor 83 as well as the transistor 73 are turned on so that the relay contact 45 as well as the relay contact 44 are turned on. Accordingly, the total electrical resistance of the reference resistor means becomes $R_C$ which is the resistance of a circuit made by connecting the reference resistors 41, 42 and 43 in parallel 1, that is, $$R_C = \frac{R41 \cdot R42 \cdot R43}{R41 \cdot R42 + R42 \cdot R43 + R43 \cdot R41} < R_B.$$

The resistance $R_C$ is set such that the voltage at the dividing point a changes between the upper and lower reference voltages $V_1$ and $V_2$.

In this manner, as the electrical resistance of the gas sensing element 21 decreases further, the resistance of the reference resistor means also decreases further and the gas composition detection by the first comparator is conducted properly in the same way as it is so made in the operating temperatures $T_2$ and $T_3$.

Thus, among the upper and lower reference voltages $V_1$ and $V_2$, and electrical resistances of the reference resistor means $R_A$, $R_B$ and $R_C$ there exists the relation $(V_2/V)R_C > R_B > (V_1/V)R_A$, $R_C > (V_1/V)R_B$ and $R_A < (V_2/V)R_B$.

After the operating temperature has risen as described above, when the operating temperature of the gas sensing element 21 drops to $T_2$, the electrical resistance R of the gas sensing element 21 shifts to a larger value. As a result, the voltage at the dividing point a becomes lower than both the upper and lower limit reference voltages $V_1$ and $V_2$ at the dividing points c and and d and the comparators 52 and 53 produce the "1" level signals.

Accordingly, the flip-flop 80 receives the "0" level signal at the set terminal S and the "1" level signal at the reset terminal R and the flip-flop 80 produces the "0" level output from the output terminal Q.

On the other hand, the flip-flop 67 receives the "0" signal at the set terminal S and also at the reset terminal R and the "1" level signal at the clock terminal CL and the "0" level signal from the terminal Q of the flip-flop 80 at the data terminal D. Since there is a slight time delay from the rise of the signal applied to the clock terminal CL of the flip-flop 80 from the "0" level to the "1" level before the Q output of the flip-flop 80 is inverted from the "1" level to the "0" level and the inverted output is applied to the data terminal D, the flip-flop 67 continues to produce the "1" level output from the terminal Q.

Accordingly, only the transistor 73 is turned on to turn on only the relay contact 44, therefore, the total electrical resistance of the reference resistor means becomes $R_B$.

As the total resistance of the reference resistor means becomes $R_B$, the voltage at the dividing point a becomes higher than the lower limit reference voltage $V_2$ at the dividing point d and the output of the third comparator 53 is inverted to the "0" level, however the flip-flop 80 continues to produce the "0" level signal because the signal being applied to the clock terminal CL does not change.

Thereafter, if the operating temperature of the gas sensing element 21 drops from $T_2$ to $T_3$, the electrical resistance of the gas sensing element 21 increases further. As a result, the voltage at the dividing point a again becomes lower than the lower limit voltage $V_2$ at the dividing point d and the third comparator 53 again produces the "1" level signal.

Accordingly, a signal rising from the "0" level to the "1" level is applied to the clock terminal CL of the flip-flop 67 and the "0" level signals are applied to the set terminal S, the reset terminal R and the data terminal D, therefore, the input terminal to the data terminal D, that is, the "0" level signal is outputted from the terminal Q.

Consequently, the transistor 73 as well as the transistor 83 are turned off and the relay contacts 44 and 45 are both turned off and the total electrical resistance of the reference resistor means becomes $R_A$.

In this manner, the reference resistance changes in accordance with the rise and fall of the operating temperature of the gas sensing element 21 and a proper gas detection is always assured.

Figure 5:
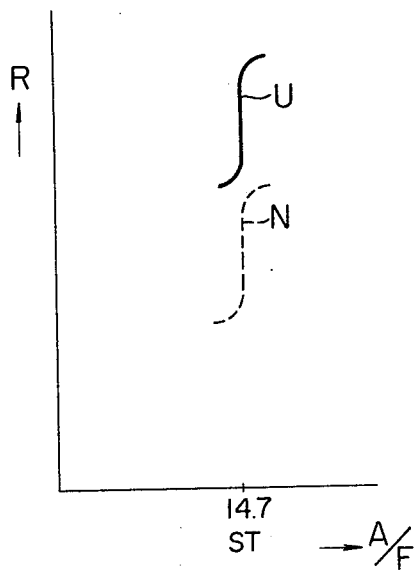

The electrical resistance characteristic of the gas sensing element 21 may change by the lapse of time as shown by a curve N (for the new product) and a curve U (for the used product whose electrical resistance is changed by the lapse of time) shown in FIG. 5, even if the operating temperature of the gas sensing element is the same. In such a case also, the reference resistance changes following the change of the electrical resistance characteristic, therefore, it is possible to carry out a proper gas detection.

Figure 6:
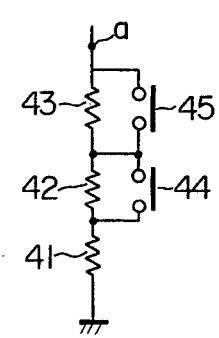
FIGS. 6 and 7 are electrical circuit diagrams showing essential parts of other embodiments of the control circuit respectively.

While the reference resistors 41, 42 and 43 are connected in parallel in the above embodiment, they may be connected in series using the normally open relay contacts 44 and 45, as shown in FIG. 6. Further, while in the above embodiment it is so made that the relay contacts are switched sequentially, they may be controlled such that when one of the relay contacts is turned on the other relay contact is turned off.

Figure 7:
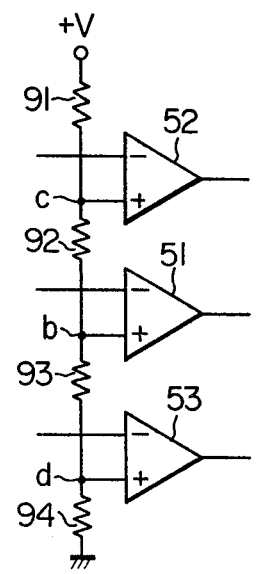

The upper and lower limit reference voltages $V_1$ and $V_2$ of the second and third comparators 52 and 53 may be decided such that the center reference voltage $V_0$ of the first comparator 51 becomes the middle value between $V_1$ and $V_2$, and the reference voltages may be appropriately set depending on the width of change of the resistance of the element used. The reference voltages $V_0$, $V_1$ and $V_2$ may be supplied by connecting resistors 91 to 94 as shown in FIG. 7.

While in the above embodiments it has been described with respect to the gas sensing in the engine with the carburetor, the present invention can also be applied to an engine with a fuel jetting device or an engine with a secondary air supply device and it can also be applied to detect exhaust gas of other combustion systems such as a boiler, etc.

We claim:

1. In a system for controlling the air-fuel ratio applied to a combustion engine by detecting the oxygen content in the exhaust gases, said system including a resistive-type oxygen responsive element connected to a voltage source in series with resistance means for producing an electric output corresponding to the resistance of said oxygen responsive element, a circuit responsive to said output signal for compensating for the dependency of the output signal of the oxygen responsive element on the environment, said circuit comprising:
   first comparison means for comparing said electric output of said oxygen responsive element with a first predetermined value;
   second comparison means for comparing said electric output of said oxygen responsive element with a second predetermined value;
   resistance control means responsive to output signals of said first and second comparison means for controlling the resistance of said resistance means so that said electric output of said oxygen responsive element varies between said first and second predetermined values of said first and second comparison means to remove at least some of the variation of said electric output of said oxygen responsive element due to said environmental dependency.

2. In a system for controlling the air-fuel ratio applied to a combustion engine by detecting the oxygen content in the exhaust gases, said system including a resistive-type oxygen responsive element connected to a voltage source in series with resistance means for producing an electric output corresponding to the resistance of said oxygen responsive element, a circuit responsive to said output signal for compensating for the dependency of the output signal of the oxygen responsive element on the environment, the resistance of said resistive-type oxygen responsive element becoming large when the air-fuel ratio is lean and becoming small when the air-fuel ratio is rich, and changing abruptly when the air-fuel ratio is stoichiometric ratio ST, said circuit comprising:
   detecting means for detecting the level of said electric output of said oxygen responsive element; and
   resistance control means responsive to an output signal of said detecting means for automatically varying the resistance of said resistance means in the same direction as variations in the resistance of said oxygen responsive element due to said environmental dependency to remove at least some of the variation of said electric output of said oxygen responsive element due to said environmental dependency.

3. In a system for controlling the air-fuel ratio applied to a combustion engine including a resistive-type oxygen responsive element disposed in the exhaust gases of said engine, and connected to a voltage source in series with resistance means for producing an output signal corresponding to the resistance of said oxygen responsive element, first comparison means for comparing said output signal of said oxygen responsive element with a first predetermined value, and mixture control means for controlling the air-fuel ratio of mixture supplied to said combustion engine in response to the output signal of said first comparison means, an apparatus for compensating the dependency of said output signal of said oxygen responsive element on the environment comprising:

second comparison means for comparing said output signal of said oxygen responsive element with a second predetermined value higher than said first predetermined value;

third comparison means for comparing said output signal of said oxygen responsive element with a third predetermined value lower than said first predetermined value; and resistance control means for controlling, in response to the output signals of said second and third comparison means, the resistance value of said resistance means to maintain said oxygen responsive element output signal between said second and third predetermined values.

* * * * *